United States Patent [19]

Miller

[11] Patent Number: 5,133,458

[45] Date of Patent: Jul. 28, 1992

[54] AMPULE-TYPE INHALANT DISPENSER

[75] Inventor: Frederic D. Miller, Rockford, Ill.

[73] Assignee: Siebe North, Inc., Charleston, S.C.

[21] Appl. No.: 678,749

[22] Filed: Apr. 1, 1991

[51] Int. Cl.⁵ .............................................. B65D 83/04
[52] U.S. Cl. ................................... 206/530; 206/813; 128/203.21
[58] Field of Search .............................. 206/530, 813; 128/203.21

[56] References Cited

U.S. PATENT DOCUMENTS

| | | | |
|---|---|---|---|
| 2,395,109 | 2/1946 | Fonda | 206/530 X |
| 2,546,848 | 3/1951 | Bishop | 206/530 |
| 3,856,142 | 12/1974 | Vessalo | 206/530 |
| 3,881,634 | 5/1975 | Thruh | 128/203.21 |
| 4,342,395 | 8/1982 | Brown | 206/530 |

FOREIGN PATENT DOCUMENTS 18518 of 1905 United Kingdom ............... 206/530

*Primary Examiner*—William I. Price
*Attorney, Agent, or Firm*—Abelman Frayne & Schwab

[57] ABSTRACT

An ampule-type inhalant dispenser is disclosed, and the manner in which it can be formed, in which shards of glass produced upon fracturing of the ampule are maintained in substantial parallelism with a mutually presented face of enveloping packaging material in order to prevent the sharp edges of the shards from piercing the packaging material, with consequent hazard to the fingers of the user.

6 Claims, 2 Drawing Sheets

AMPULE-TYPE INHALANT DISPENSER

FIELD OF THE INVENTION

This invention relates to inhalant dispensers of the type comprised by a frangible glass ampule containing a measured quantity of a volatile inhalant, such as an ammonia inhalant. Ampules of this type commonly are encased in a wrapping or packaging of an absorbent material that is resistive to shards of glass produced upon manual crushing or fracturing of the contained ampule.

BACKGROUND OF THE INVENTION

Ampules of this type are formed from an extremely thin glass, commonly known as onion-skin glass, and are well known in the art, as is the need to encapsulate such ampules within a material that is pervious to the liquid contained within the ampule, but, which is highly resistive to puncturing by shards of glass produced upon manual fracturing of the ampule. Fracturing of the ampule is required in order to permit dispersion of the inhalant into the encapsulating material for subsequent volatilization and inhalation by a person in need of a stimulant.

Prior proposals have been to provide a closed packet within which the ampule is confined, and within which the ampule is loosely movable, the packet being formed from a material such as a scrim of natural or synthetic fibers, which acts to contain the shards of glass produced upon fracturing of the ampule. A construction of this type is disclosed in Thrun U.S. Pat. No. 3,881,634 issued May 6, 1975.

Other proposals, such as in Brown U.S. Pat. No. 4,342,395, issue Aug. 3, 1982, Fonda U.S. Pat. No. 2,395,109, issued Feb. 19, 1946 and Bishop U.S. Pat. No. 2,546,848 issued Aug. 3, 1982, have required the encapsulation of the ampule within a sleeve or tube that is formed from a material substantially impervious to the glass shards, and which on the other hand will provide for absorption of the inhalant liquid for its subsequent volatilization as an inhalant. Brown teaches an ampule that is closely embraced within a packet of absorbent scrim material, and which immobilizes the ampule within the packet prior to fracturing of the ampule.

Proceeding from Thrun and Brown, it is at the time that the ampule is fractured that the major problem with such inhalant dispensers occurs. Upon fracturing of the glass ampule, the wall of the ampule disintegrates into shards of glass, which are free to move in an entirely random manner within the cavity in the packet. Orientation of the glass shards perpendicular to the inner wall of the packet can occur, in which position the shards act substantially in the manner of razor blades, and are capable of cutting through the material forming the packet, with the result of embedment of the ends of the glass shards into the finger tips of the user, and cutting of the users' finger tips. If the cuts become dampened or saturated with the ammonia liquid, this can enter the cuts and cause severe discomfort to the user.

OBJECT OF THE INVENTION

It is the object of this invention to eliminate this particular problem of the known ampule type inhalant dispensers.

SUMMARY OF THE INVENTION

According to the present invention, the exterior surface of the glass ampule is adhesively connected to the inner surface of the packaging scrim material forming the packet. The adhesive bonds the radially outer surfaces of the ampule to the interior surface of the packaging material, such that glass shards, when formed, are caused to remain in parallelism with the inner surface of the packaging material, thus precluding orientation of the glass shards in a direction perpendicular to the inner surface of the packaging material.

In this manner, the chances of perforation of the packaging material by the glass shards is eliminated in its entirety, the glass shards being incapable of movement within the packaging material upon the formation of those glass shards.

Preferably, the adhesive is a hot melt adhesive that remains in a soft rubber-like condition at ambient temperatures. Such adhesives commonly are employed in the food packaging industry in the securement of labels or wrappers to cans and bottles. Typical of such hot melt adhesives is the one sold under the registered trademark DISPOMELT, and which is manufactured by the Adhesives Division of National Starch and Chemical Corporation. At its melting temperature, that adhesive becomes pressure sensitive, thus permitting the outer surface of the ampule to be adhesively secured and positionally bonded to the inner surface of the packaging material. At ambient temperatures, the adhesive assumes a pliable rubber-like consistency, that provides an extremely strong bond with the glass ampule, while at the same time remaining flexible and pliable.

This invention also provides a method of manufacturing the ampule-type inhalant dispensers of the invention by mass-production techniques.

According to the method of the present invention, the formed and sealed ampules are deposited serially onto a continuously moving tape of scrim material that has been coated with heated hot melt adhesive immediately prior to the depositing of the glass ampules on the surface thereof. The adhesive, under these conditions is tacky and pressure sensitive. The glass ampules thus are immediately adhesively attached to the surface of the moving tape in a manner immobilizing the ampules against movement in the axial direction of the tape, or, rolling laterally of the tape.

Immediately after depositing of the glass ampules onto the tape coated with the heated hot melt adhesive, the lateral sides of the tape are displaced upwardly, and are caused to wrap completely around the entire circumference of the glass ampules, the edges of the tape then forming a butt or lap joint extending longitudinally of the tape. The tape is attached completely to and entirely covers the outer surface of the ampules leaving no part of the exterior surface of the glass ampule uncovered, other than at the axial ends thereof.

While the hot melt adhesive is still sufficiently heated, the travelling length of assembled ampules and tape is then subjected to a lateral clamping and cutting operation, which draws the adhesively coated tape into intimate contact with the glass ampules at their axial ends, thus providing a bond between the tape of wrapping material and the axial ends of the ampules.

When so formed, the glass ampules are totally encased within the tape of wrapping material and are adhesively bonded throughout their entire external surface to the inner surface of the wrapping tape. The ampules are thus immobilized within the packet formed by the wrapping tape, and are protected in a manner that mitigates the possibility of accidental fracturing of the ampule by rough handling of the dispenser prior to its actual use.

Conveniently, a tape bearing identifying indicia can be applied to the outer surface of the travelling packaging tape by the use of a suitable adhesive, or, the packaging tape can be pre-printed with such indicia.

The packaging tape itself can be formed of any suitable material, preferably a scrim material, formed from natural or synthetic fibers that have been felted into each other to provide a stable, structurally strong fabric material that is resistive to tearing or ripping at the time the ampule is fractured. Common manners of fracturing the ampule are by either by crushing the ampule between a user's fingers, or, by breaking the ampule by the application of oppositely directed forces exerted at spaced positions longitudinally of the ampule.

DESCRIPTION OF THE DRAWINGS

The invention will now be described with reference to the accompanying drawings, which illustrate a preferred embodiment of the invention, and, in which.

DESCRIPTION OF THE PREFERRED EMBODIMENTS

Figure 1:
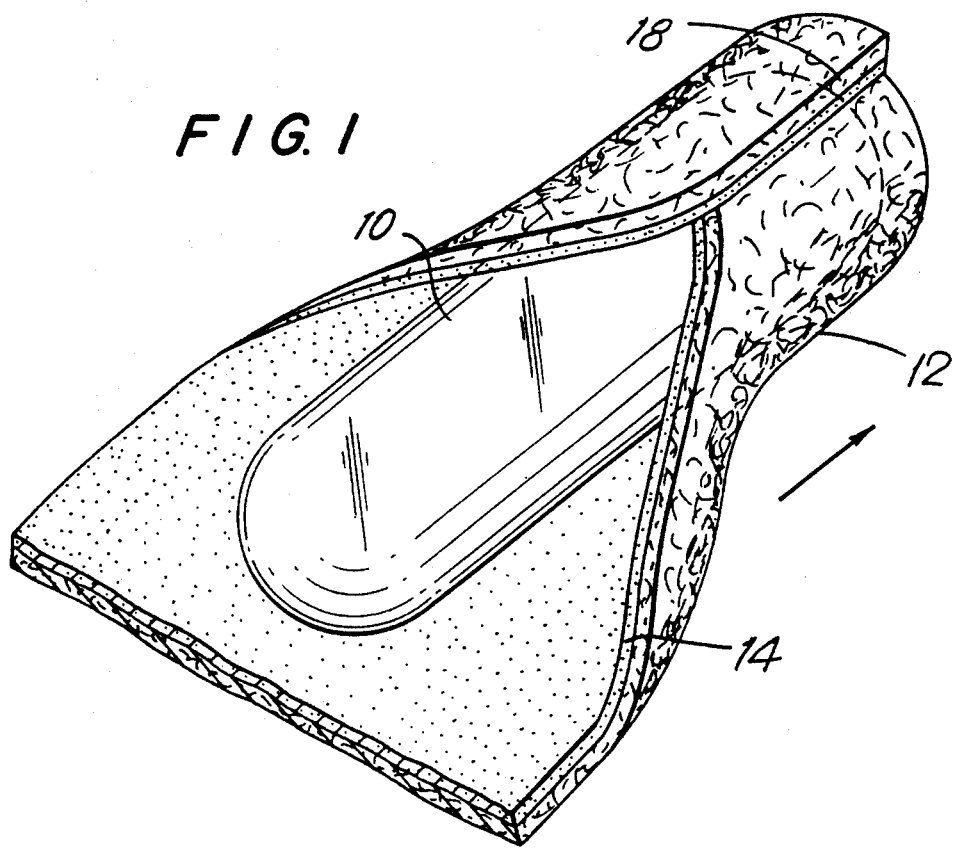
FIG. 1 is a perspective view of an ampule-type inhalant dispenser according to the present invention, while in the process of assembly.

Referring firstly to FIG. 1, an ampule-type inhalant dispenser is shown in the process of assembly. In FIG. 1, a glass ampule 10 containing, for example, an ammonia inhalant has been pre-formed in any conventional manner, and, has been deposited on a continuous tape 12 of a scrim material. The scrim material can be formed from natural or synthetic fibers, or admixtures thereof, which have been felted to provide the scrim in any known manner.

Figure 2:
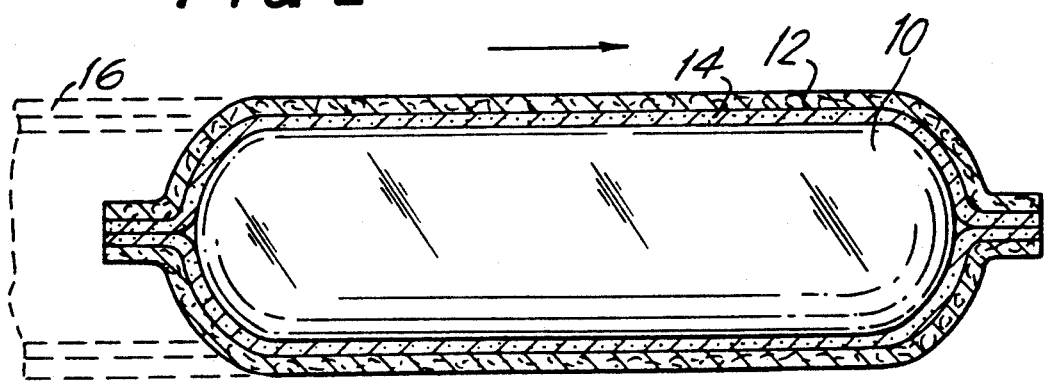
FIG. 2 is a longitudinal cross-section through the dispenser of the invention when in a completed form; and, FIG. 3 is a diagrammatic representation of the method of forming the ampule-type inhalant dispenser of the present invention.

Prior to the ampule 10 being deposited on the tape 12, the tape 12 has been coated with a hot melt adhesive indicated at 14. The hot melt adhesive is in a heated condition at the time the glass ampule 10 is deposited thereon, the hot melt adhesive at the time being pressure sensitive, such that the glass ampule is tacked to the tape 12 of scrim material prior to the tape 12 being wrapped around the outer periphery of the glass ampule 10. That operation can be performed in any conventional manner, such as by drawing the assembled ampule and tape through a folding horn. After having passed through the folding horn, the tape 12 will have been formed into a continuous cylindrical form, as indicated by the chain dotted lines 16 in FIG. 2, and, the edges of the tape 12 will have moved into abutting or overlying relationship to provide a continuous joint 18 extending longitudinally of the assembly. The joint 18 can be a butt joint, but, more preferably, it is a lap joint in which one edge of the travelling tape has been overlaid with the other edge of the travelling tape, in order to ensure that there are no discontinuities in the ultimate packaging of the glass ampule.

The wrapping of the glass ampule 10 is carried out in a rapid and continuous manner, such that after emerging from the circumferential wrapping process, the hot melt adhesive 14 still retains its pressure sensitive capabilities. Immediately after the longitudinal wrapping of the ampule 10, the tape 12, those portions of the tape that extend beyond the glass ampule are pinched or crimped, in order to provide a secure interconnection between the opposed internal faces of the then tubular form of the tape 12, and, the tape is cut into appropriate lengths.

The assembly is then permitted to cool, the heated hot melt adhesive 14 then going through a transition in which it develops extremely strong adhesive properties, while at the same time remaining pliable.

The resulting structure is one in which the entire outer circumference of the glass ampule 10 has been provided with a continuous coat of the hot melt adhesive, and, the packaging provided by the scrim tape 12 has been edge and end secured in a manner that defies attempts at manual disassembly of the packaging from the outer surface of the glass.

If, now, one breaks the glass ampule by crushing it between ones' fingers, or, by snapping it longitudinally, then, any shards of glass resulting from fracture of the glass ampule remain firmly adhered to the inner face of the tape 12, and, are immobilized against moving into a direction in which their sharp edges extend perpendicular to the tape. As the glass shards are immobilized in the same plane as the inner surface of the tape, they are, thus, incapable of piercing the scrim tape 12, and, the possibility of the glass shards becoming impaled or embedded in the users' fingers, with possible laceration of the user's fingers, is eliminated in its entirety.

This protective capability further extends to mishandling of the assembly prior to use, exactly the same conditions arising in the event that the glass ampule is fractured by an impact or by rough handling.

An added benefit to protecting the user's fingers against laceration is that should the user's fingers become moistened by the ammonia liquid upon intentional fracturing of the glass ampule, the user is spared the acute discomfort of the ammonia liquid entering a laceration in the user's fingers.

Figure 3:
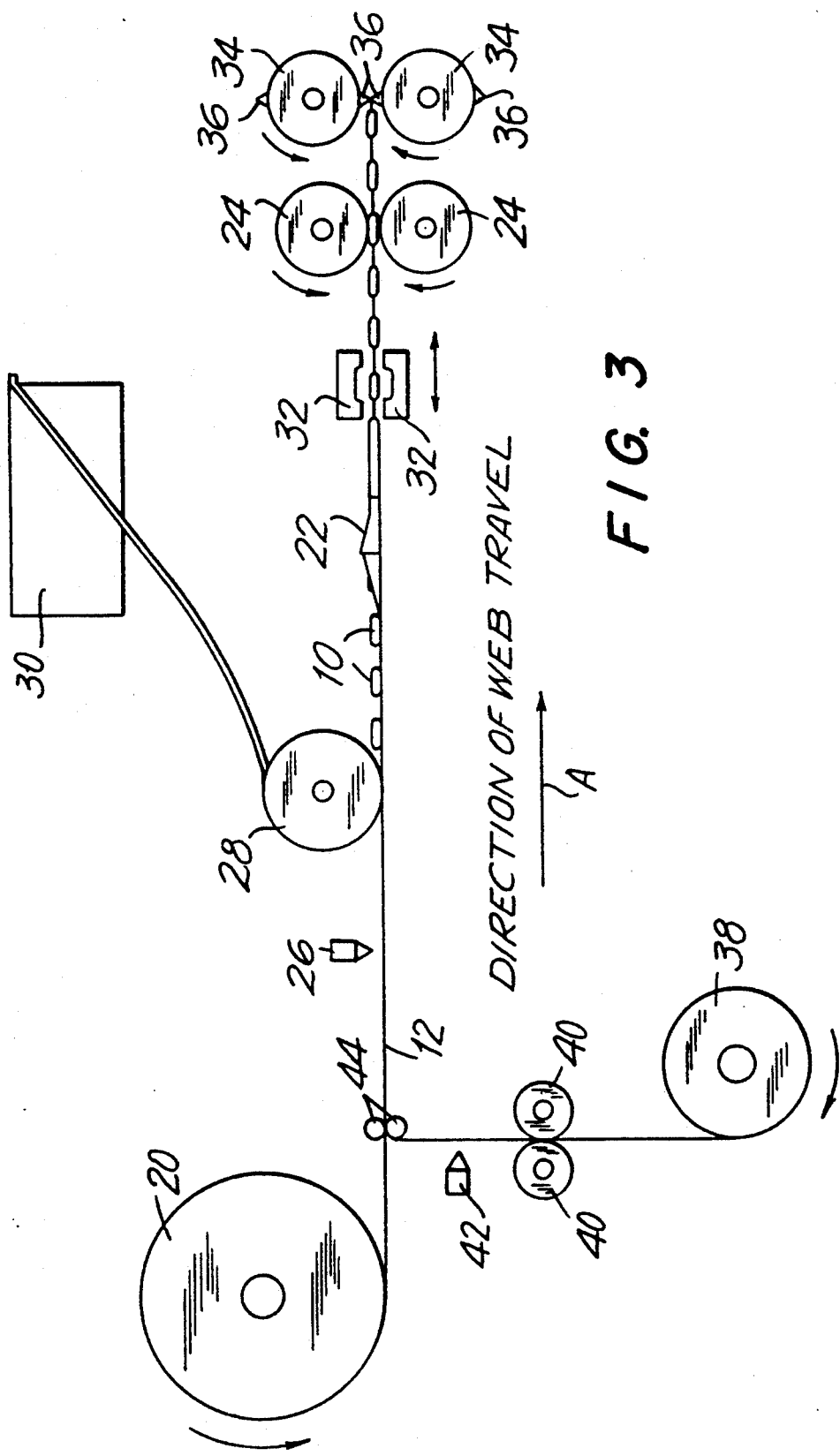

The ampule-type inhalant dispenser of the present invention can be manufactured in a continuous process and at very high production rates by employing the process illustrated in FIG. 3.

In FIG. 3, a roll of scrim tape 20 is continuously pulled through a tubular folding horn 22 by traction rollers 24, the direction of web travel being indicated by the arrow A.

Prior to reaching the folding horn 22, a film or layer of hot melt adhesive in a heated condition is applied to the upper surface of the tape by an adhesive applicator 26 of any known form. Immediately thereafter, and while the hot melt adhesive is still heated and pressure sensitive, the glass ampules 10 are deposited thereon in axially spaced relation. Any known form of escapement mechanism 28 can be employed that is supplied with the glass ampules in serial relation from a storage bin 30.

Immediately after passing through the folding horn 22, and while the hot melt adhesive is still heated and active, the tubular assembly is passed through a clamping or crimping unit 32 in which those portions of the tape 12 that extend beyond the ends of the glass ampule are forced into intimate contact with each other under a clamping or crimping pressure. The assembly then passes through the traction rollers 24 and progresses to a second pair of traction rollers 34 provided with cutting blades 36, which sever the assembled tape and ampules into individual units. The traction rollers are formed from a relatively soft elastomeric material, and act to compress the tape into intimate engagement with the outer surface of the ampule.

If desired, the tape 12 progressing from the roll 20 can be pre-printed or embossed with identification of the contents of the ampules, or, and as illustrated in FIG. 3, an identification tape can be applied to the reverse side of the tape 12, again by using a hot melt adhesive. The identification tape is stored on a roll 38, and is drawn through tensioning rollers 40 prior to the application of the hot melt adhesive to one side of the identification tape by an adhesive dispenser 42. The coated identification tape and the scrim tape 12 are then passed through pressure rollers 44, which conveniently can be embossing rollers, at which point the identification tape becomes firmly attached to the lower surface of the tape 12. Conveniently, the rollers 44 are capable of dissipating heat, such that the hot melt adhesive applied by the adhesive dispenser 42 is cooled to its rubber like state prior to the composite tape reaching the adhesive dispenser 26. The tape 12 and the identification tape 38, thus are united to each other prior to the tape 12 entering the folding horn 22, thus facilitating the folding stage.

While the wrapping steps have been illustrated in FIG. 3 as being a progression along a linear horizontal path, it will, of course, be appreciated that the various stages can be arranged in any other orientation provided that a continuous flow path is maintained.

While the invention has been described with reference to the use of hot melt adhesives, it will be understood that the invention is not limited to the use of such hot melt adhesives. Any other suitable adhesives can be employed that is pressure sensitive at the time the ampules are deposited onto the tape 12, wrapped into tubular form, and then compacted and severed into individual units, provided that the pressure sensitive adhesive remains sufficiently strong and flexible to prevent the wrapping tape 12 from disassembling from the ampule 10 by unwrapping from the ampule. In this respect, adhesives that employ a volatile solvent agent that increase in bonding strength upon vaporization of the solvent can be employed in substitution for a hot melt adhesive.

I claim:

1. An ampule-type inhalant dispenser, of the type including an ampule of a thin glass and which contains a quantity of a volatile inhalant, and a packaging for said ampule comprised of an absorbent packaging material, further including:

a coating of an adhesive of rubber-like consistency that remains flexible at ambient temperatures interposed between substantially the entire outer surface of said ampule and substantially the entire mutually presented surface of said packaging material, said coating being operative to adhere shards of glass produced upon fracturing of said ampule to said mutually presented surface of said packaging material, said packaging material enveloping said ampule and being adhered thereto by said adhesive over substantially the entire extent of the outer surface of said ampule.

2. The ampule-type inhalant dispenser of claim 1, in which said packaging material is in the form of a tape that has been wrapped around said ampule, and which provides a continuous covering extending over the entire outer surface of said ampule.

3. The ampule-type inhalant dispenser of claim 1, in which said packaging material is in the form of a tape oriented to extend axially of said ampule, opposite side edges of said tape extending into at least butting relationship about said ampule, opposite ends of said tape being adhered to each other to produce a complete enclosure enveloping said ampule.

4. The ampule-type inhalant dispenser of claim 3, in which said side edges of said tape are overlapped to provide a lap joint extending continuously in the axial direction of said ampule.

5. The ampule-type inhalant dispenser of claim 1, in which said adhesive is a hot melt adhesive that exhibits pressure sensitive characteristics when heated.

6. The ampule-type inhalant dispenser of claim 1, in which said adhesive is pressure sensitive at the time of assembly of said dispenser, and progressively hardens into a flexible rubber-like material.

* * * * *